United States Patent
Ikeda

(10) Patent No.: US 10,420,573 B2
(45) Date of Patent: Sep. 24, 2019

(54) SURGICAL TOOL

(71) Applicant: OLYMPUS CORPORATION, Tokyo (JP)

(72) Inventor: Hiromu Ikeda, Tokyo (JP)

(73) Assignee: Olympus Corporation, Tokyo (JP)

( * ) Notice: Subject to any disclaimer, the term of this patent is extended or adjusted under 35 U.S.C. 154(b) by 134 days.

(21) Appl. No.: 15/661,065

(22) Filed: Jul. 27, 2017

(65) Prior Publication Data

US 2017/0319223 A1    Nov. 9, 2017

Related U.S. Application Data

(63) Continuation of application No. PCT/JP2015/083641, filed on Nov. 30, 2015.

(30) Foreign Application Priority Data

Feb. 2, 2015  (JP) .................................. 2015-018368

(51) Int. Cl.
*A61B 17/28* (2006.01)
*A61B 17/02* (2006.01)
(Continued)

(52) U.S. Cl.
CPC ...... *A61B 17/2812* (2013.01); *A61B 17/0218* (2013.01); *A61B 17/083* (2013.01); *A61B 17/10* (2013.01); *A61B 34/71* (2016.02); *A61B 90/06* (2016.02); *A61B 17/1227* (2013.01); *A61B 17/1285* (2013.01); *A61B 2017/00017* (2013.01); *A61B 2017/00473* (2013.01);
(Continued)

(58) Field of Classification Search
CPC ......... A61B 17/00; A61B 17/28; A61B 17/29; A61B 17/30; A61B 17/2909; A61B 17/2812; A61B 2017/00017
See application file for complete search history.

(56) References Cited

U.S. PATENT DOCUMENTS

| 5,938,678 A | 8/1999 | Zirps et al. |
| 6,139,563 A | 10/2000 | Cosgrove, III et al. |
(Continued)

FOREIGN PATENT DOCUMENTS

| EP | 2 305 144 A1 | 4/2011 |
| JP | 2000-33071 A | 2/2000 |
(Continued)

OTHER PUBLICATIONS

Extended Supplementary European Search Report dated Oct. 1, 2018 in European Patent Application No. 15 88 1192.7.
(Continued)

*Primary Examiner* — Vi X Nguyen
(74) *Attorney, Agent, or Firm* — Scully Scott Murphy & Presser, P.C.

(57) ABSTRACT

The surgical tool (1) is including a main unit (2) including a case (21) and a hollow shaft (22) provided on the case (21), a holder assembly (3) that holds a living tissue (T) in the body cavity, a connector (4) that connects the main unit (2) inserted through the shaft (22) to the holder assembly (3), an operating unit (5) that is provided on the main unit (2) to allow the connector (4) to enter or leave the shaft (22) and a tension adjustor (6) capable of adjusting the tension of the connector (4).

5 Claims, 17 Drawing Sheets

(51) Int. Cl.
- A61B 17/08 (2006.01)
- A61B 17/10 (2006.01)
- A61B 34/00 (2016.01)
- A61B 90/00 (2016.01)
- A61B 17/00 (2006.01)
- A61B 17/122 (2006.01)
- A61B 17/128 (2006.01)
- A61B 17/29 (2006.01)

(52) U.S. Cl.
CPC ............ *A61B 2017/00991* (2013.01); *A61B 2017/0287* (2013.01); *A61B 2017/2901* (2013.01); *A61B 2017/2905* (2013.01); *A61B 2034/715* (2016.02); *A61B 2090/064* (2016.02)

(56) References Cited

U.S. PATENT DOCUMENTS

| | | |
|---|---|---|
| 6,352,503 B1 | 3/2002 | Matsui et al. |
| 9,649,015 B2 | 5/2017 | Okada |
| 2003/0191494 A1 | 10/2003 | Gray et al. |
| 2011/0288579 A1 | 11/2011 | Hyodo |
| 2015/0012021 A1 | 1/2015 | Mihara |
| 2015/0209059 A1* | 7/2015 | Trees ............... A61B 18/1445 606/170 |
| 2016/0029875 A1 | 2/2016 | Okada |

FOREIGN PATENT DOCUMENTS

| | | |
|---|---|---|
| JP | 2002-503131 A | 1/2002 |
| JP | 2006-341111 A | 12/2006 |
| JP | 2010-075375 A | 4/2010 |
| JP | 2011-239922 A | 12/2011 |
| WO | WO 2014/199759 A1 | 12/2014 |
| WO | 2015/012179 A1 | 1/2015 |

OTHER PUBLICATIONS

International Search Report dated Feb. 23, 2016 issued in PCT/JP2015/083641.

* cited by examiner

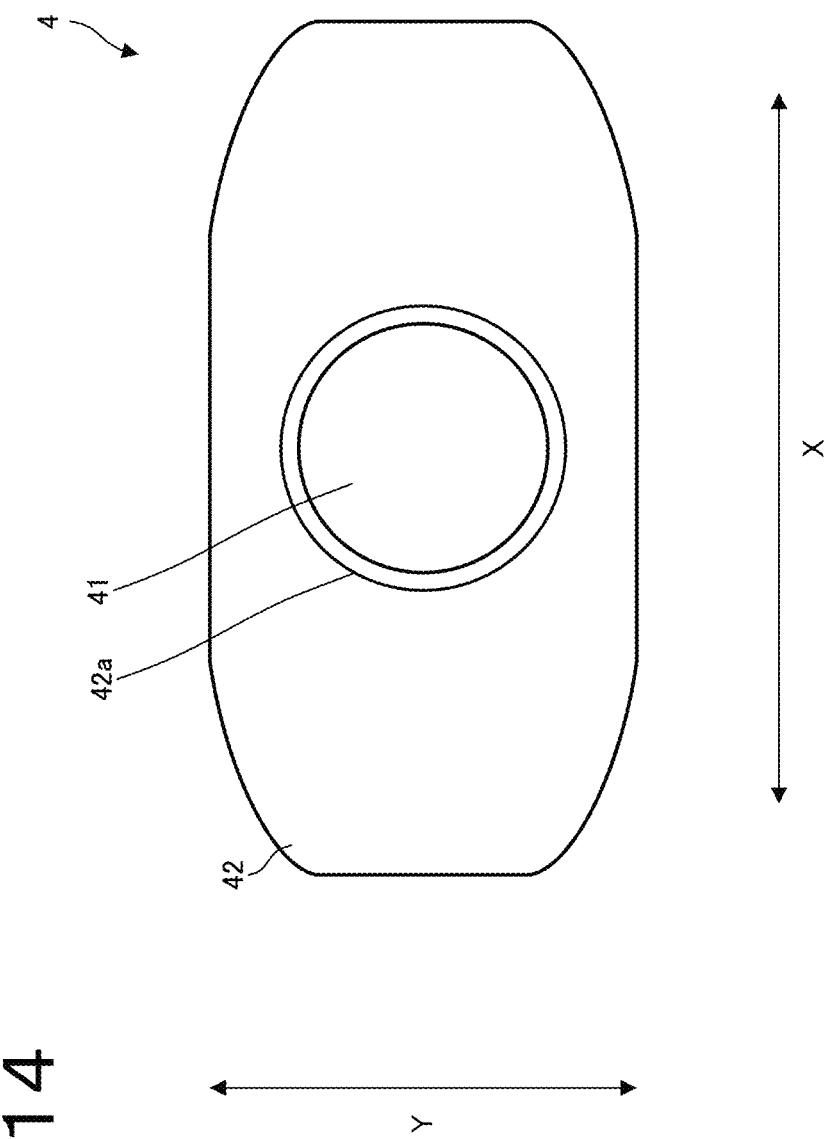

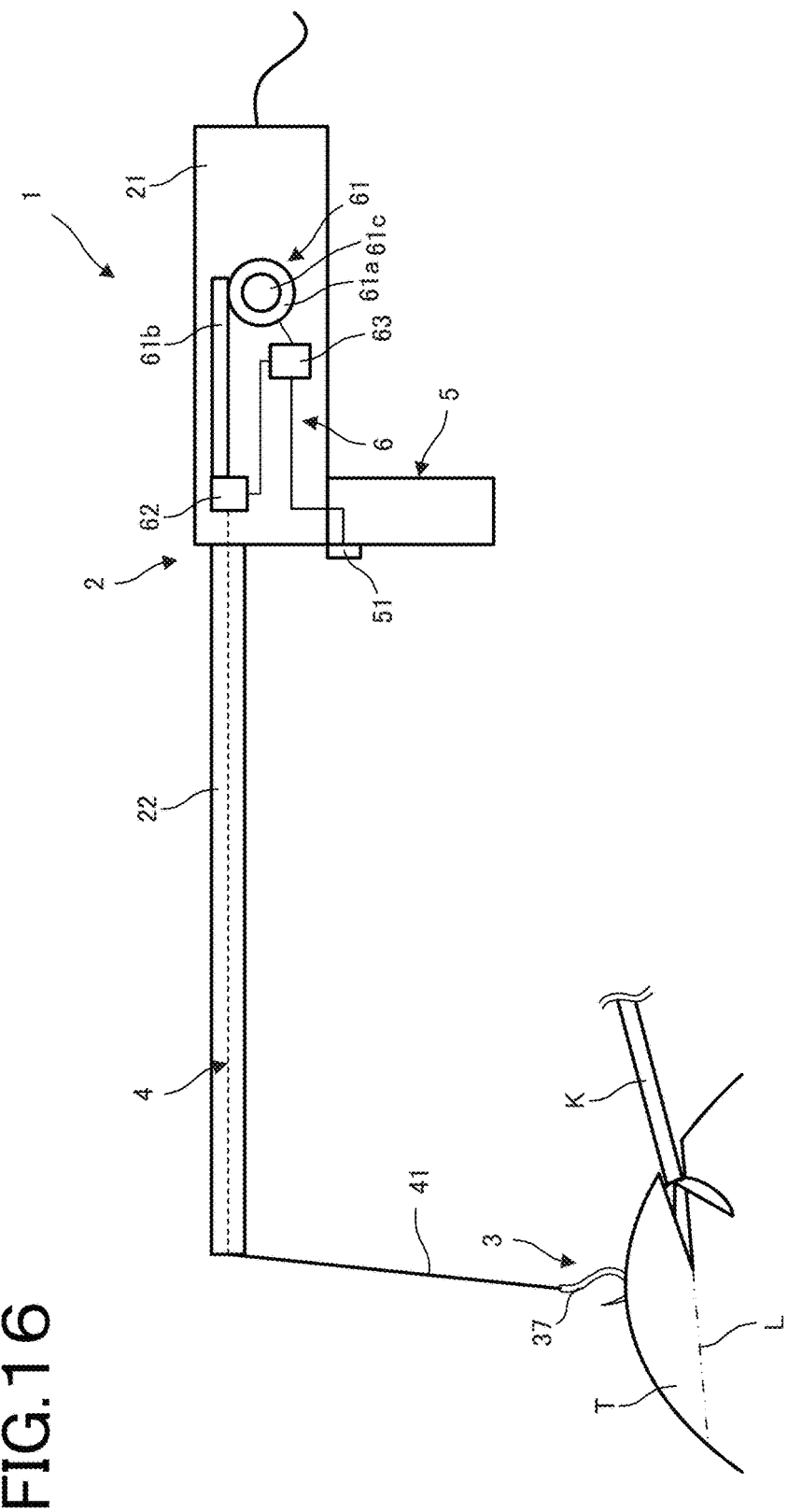

SURGICAL TOOL

CROSS-REFERENCE TO RELATED APPLICATIONS

This application is a continuation claiming priority on the basis of Japan Patent Application No. 2015-018368 applied in Japan on Feb. 2, 2015 and based on PCT/JP2015/083641 filed on Nov. 30, 2015. The contents of both the PCT application and the Japan Application are incorporated herein by reference.

BACKGROUND OF THE INVENTION AND RELATED ART STATEMENT

The present invention relates to a surgical tool capable of being inserted through a patient upon surgical operations for viewing, applying treatments, and so on.

So far there has been a medical instrument widely used in which a surgical tool is inserted through the body cavity of a patient and a distal end of the surgical tool is pulled or towed by means of a wire or the like for viewing organs within the body cavity or applying treatments to them. For operations, a plurality of surgical tools such as an endoscope for viewing purposes, forceps for taking a grip of tissues or an electric scalpel for excising off tissues are often inserted through the body cavity. A plurality of such surgical tools may be likely to interfere with one another in the close body cavity.

JP(A) 2006-341111, JP(A) 2010-075375 and Japanese Unexamined Patent Application Publication No. 2002-503131 disclose a surgical tool including a distal-end joint assembly that is flexible and bendable. If the distal end of the surgical tool is bent, it is then possible to prevent interference to some extent.

SUMMARY OF INVENTION

According to one embodiment, a surgical tool includes:
a main unit including a case and a hollow shaft provided on the case,
a holder assembly for holding a living tissue within the body cavity,
a connector that is inserted through the shaft to connect the main unit to the holder assembly, and
a tension adjustor that moves the connector relative to the shaft for adjustment of tension of the connector, wherein the tension adjustor comprises:
a tension detector that detects the tension of the connector, and
a driver that is provided on the case to drive the connector on the basis of a value detected by the tension detector.

BRIEF DESCRIPTION OF DRAWINGS

FIG. 14 is illustrative of the surgical tool according to the third embodiment.

FIGS. 15A, 5B and 5C are a view of the surgical tool according to the third embodiment as viewed from above.

FIG. 16 is illustrative of the surgical tool according to the fourth embodiment.

DESCRIPTION OF EMBODIMENTS

Specific embodiments will now be explained.

Figure 1:
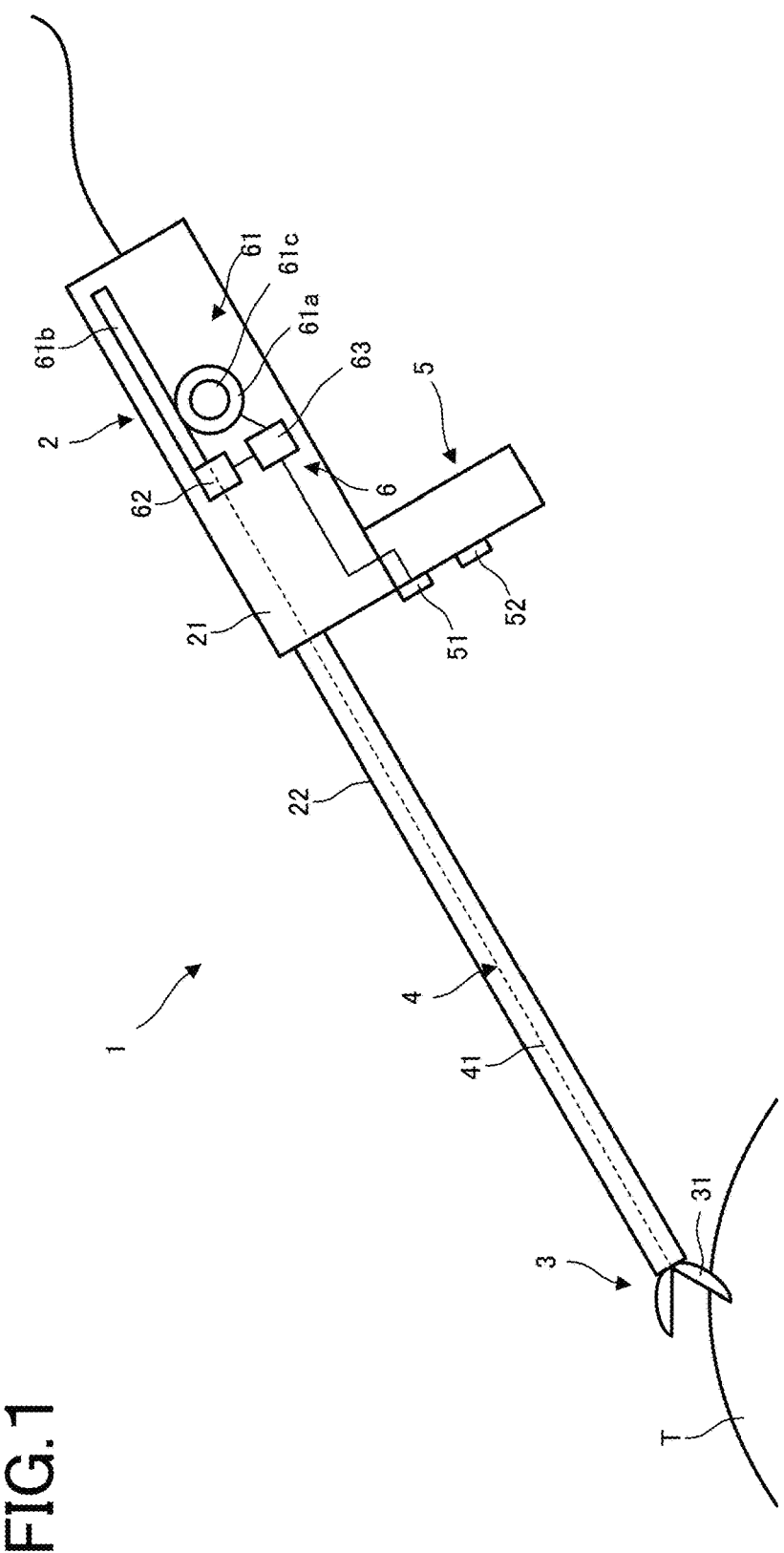
FIG. 1 shows the surgical tool according to the first embodiment.

FIG. 1 is illustrative of the surgical tool 1 according to the first embodiment of the invention.

The surgical tool 1 according to the first embodiment includes a main unit 2 including a case 21 and a hollow shaft 22 provided on the case 21, a holder assembly 3 that holds a living tissue T within the body cavity, a connector 4 that is inserted through the shaft 22 to connect the main unit 2 to the holder assembly 3, a tension adjustor 6 that moves the connector 4 relative to the shaft 22 to adjust the tension of the connector 4. The surgical tool 1 according to the first embodiment further includes an operating unit 5 for conversion to a tension holding mode in which the tension of the connector 4 is held, and the tension of the connector 4 is adjusted by the tension adjustor 6 in the tension holding mode.

The main unit 2 includes the case 21 for housing the tension adjustor 6 and so on, and the hollow shaft 22 that is provided on the case 21 for insertion through the connector 4.

The holder assembly 3 is connected to one end of the connector 4. According to the first embodiment, the holder assembly 3 includes a gripper 31 that grips a living tissue in the body cavity. The gripper 31 has a structure capable of being opened and closed by operation of a gripper opening/closing member 52.

One end of the connector 4 is attached to the holder assembly 3 while the other end of the connector 4 is attached to a moving member 61b. According to the first embodiment, the connector 4 includes a wire 41 that enters or leaves the shaft 22 as the moving member 61b moves.

The operating unit 5 includes a tension holding mode operating member 51 that is placed in the tension holding mode for conversion to the tension holding mode in which the tension of the connector 4 is held. According to the first embodiment, the operating unit 5 further includes the gripper opening/closing member 52 for operating the opening and closing of the gripper 31. According to the first embodiment, the tension holding mode operating member 51 and the gripper opening/closing member 52 are each preferably constructed of a toggle button.

The tension adjustor 6 includes a driver 61 mounted in the case 21, a tension detector 62 that detects the tension of the connector 4, and a control unit 63 that controls the driver 61 on the basis of a value detected by the tension detector 62. The tension adjustor 6 adjusts the tension of the connector 4 in the tension holding mode.

The driver 61 includes a driving member 61a held in the main unit 2, a moving member 61b that moves by virtue of a driving force of the driving member 61a, and a drive operating portion 61c made up of a dial or the like that drives the driving member 61a. According to the first embodiment, the driver 61 operates such that rotation of the driving member 61a causes rotation of a pinion so that a rack is moved as the moving member 61b. Note here the driving member 61a may be driven in response to a command signal from the control unit 63 or, alternatively, it may be done by manual rotation of the drive operating portion 61c.

The tension detector 62 is attached to the moving member 61b, and moves together with the moving member 61b. Referring to the control unit 63, the tension holding mode operating member 51 is operated for selection of the tension holding mode, whereupon the driving member 61a is controlled such that the value detected by the tension detector 62 becomes a given one.

How to operate the surgical tool 1 according to the first embodiment will now be explained.

First, the gripper 31 is inserted into the abdominal cavity through a trocar (not shown), and opened by operation of the gripper opening/closing member 52.

Figure 2:
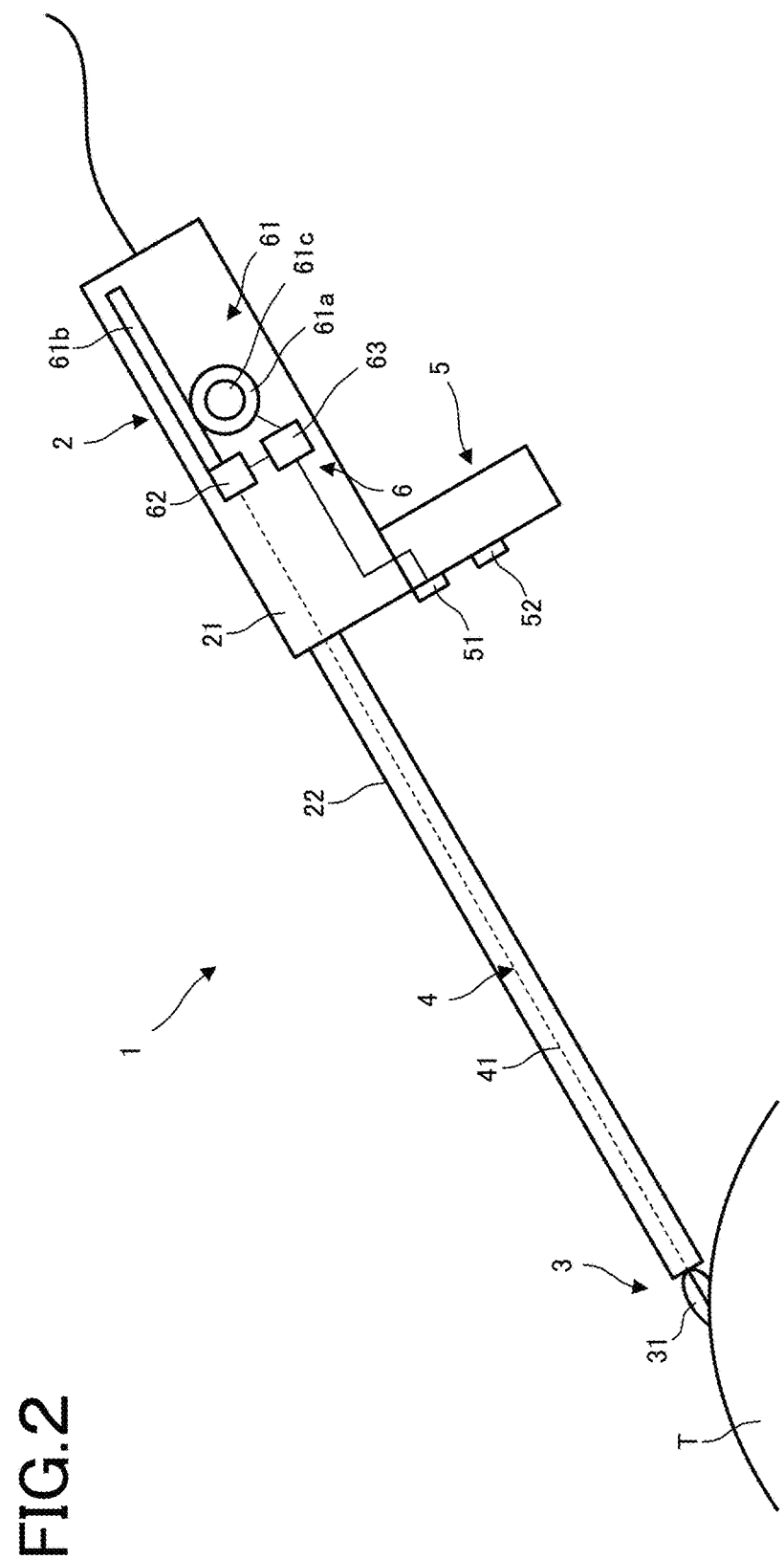
FIG. 2 shows that a tissue is being held by the surgical tool according to the first embodiment.

FIG. 2 shows that a tissue T is being held by the surgical tool 1 according to the first embodiment.

After the gripper 31 inserted through the abdominal cavity is put on the tissue to be treated in the body cavity, it is closed by operation of the gripper opening/closing member 52 to hold the tissue T as shown in FIG. 2. It is thus possible to use a simple structure to hold the tissue T by the gripper 31 unerringly.

Figure 3:
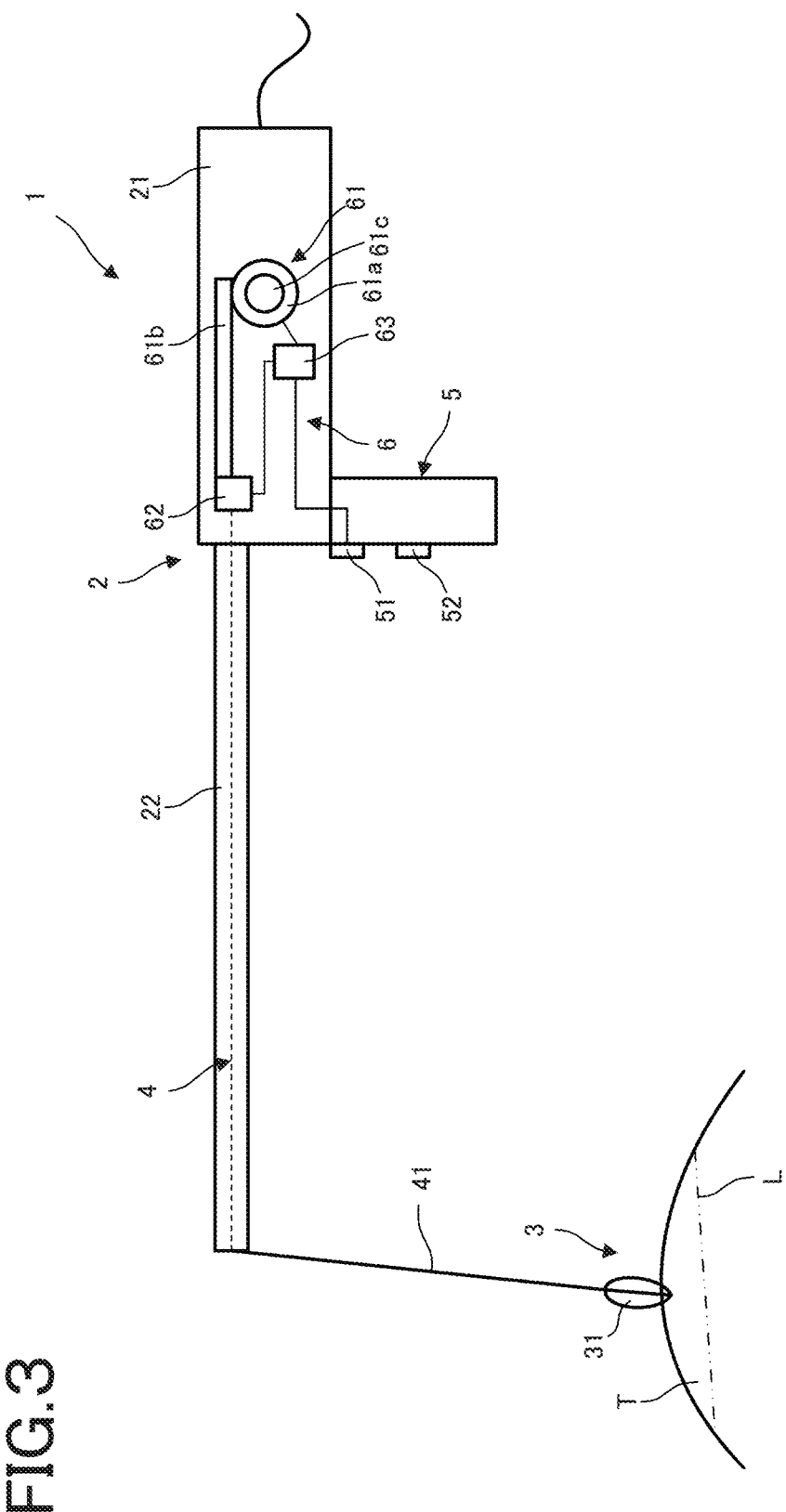
FIG. 3 shows that a tissue is being pulled by the surgical tool according to the first embodiment.

FIG. 3 shows that the tissue T is being pulled by the surgical tool 1 according to the first embodiment.

Subsequently, the wire 41 is let out while the tissue T is held by the gripper 31. To let out the wire 41, the drive operating portion 61c may be put into operation thereby rotating the driving member 61a and moving the moving member 61b.

After the wire 41 is let out, the shaft 22 is lifted upward, and the movement of the shaft 22 is stopped in a position where the peeling line L of the tissue T is identifiable through an endoscope. In that position, the tension holding mode operating member 51 is operated and placed in the tension holding mode.

Figure 4:
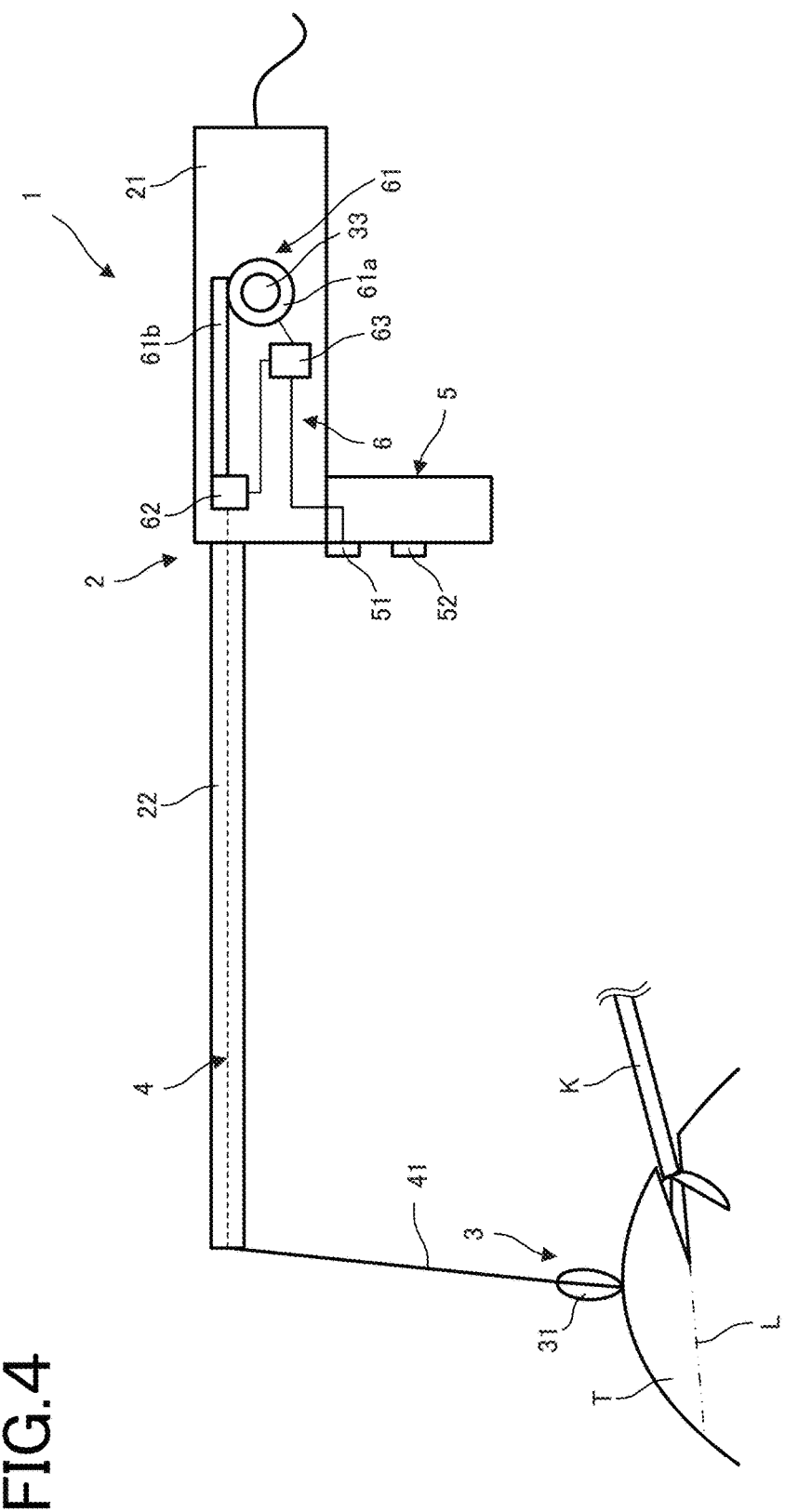
FIG. 4 shows that a tissue is being peeled off by the surgical tool according to the first embodiment.

FIG. 4 shows that the tissue T is being peeled off by the surgical tool 1 according to the first embodiment.

After the movement of the shaft 22 is stopped to place the tension holding operating member 51 in the tension holding mode, the tissue T is peeled off along the peeling line L by means of a peeling forceps K or the like. As peeling progresses while the tissue T is just only held as done in the prior art, it will cause the portion of the tissue T held by the gripper 31 to get loose, making the peeling line L less visible. With the surgical tool according to the first embodiment, the wire 41 moves through the shaft 22 as peeling progresses such that the tension of the wire 41 is kept constant and with this, the gripper 31 moves upward so that the tissue T can be pulled constantly through the wire 41 under proper tension without budging the main unit 2.

Consequently, the tissue T is gradually pulled up while peeled off with the peeling line L remaining clearly visible. It is thus possible to peel off the tissue T unerringly.

Further, the surgical tool 1 according to the first embodiment has a function of stopping the movement of the wire 41 when there is an abrupt change in the value detected by the tension detector 62. For instance, when the tension disappears abruptly at the time peeling comes to an end, it is possible to prevent abrupt movement of the gripper 31 that may otherwise lead to damages to the interior of the body cavity.

The holder assembly 3 according to the first embodiment is here explained.

Figure 5A:
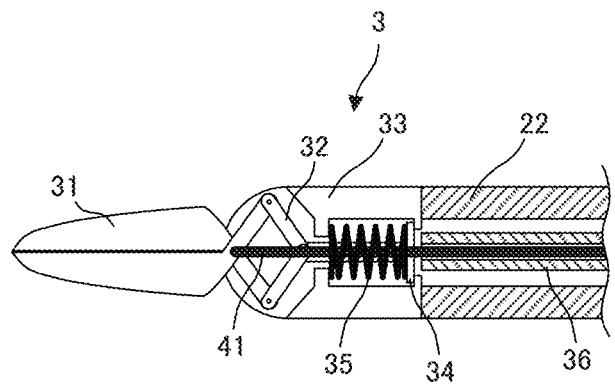
FIGS. 5A, 5B and 5C are illustrative of the holder assembly in the surgical tool according to the first embodiment.
Figure 5B:
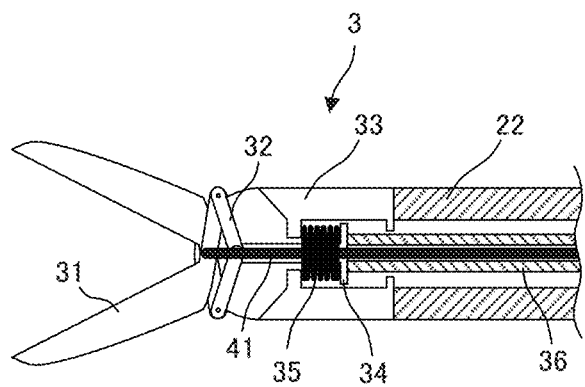
Figure 5C:
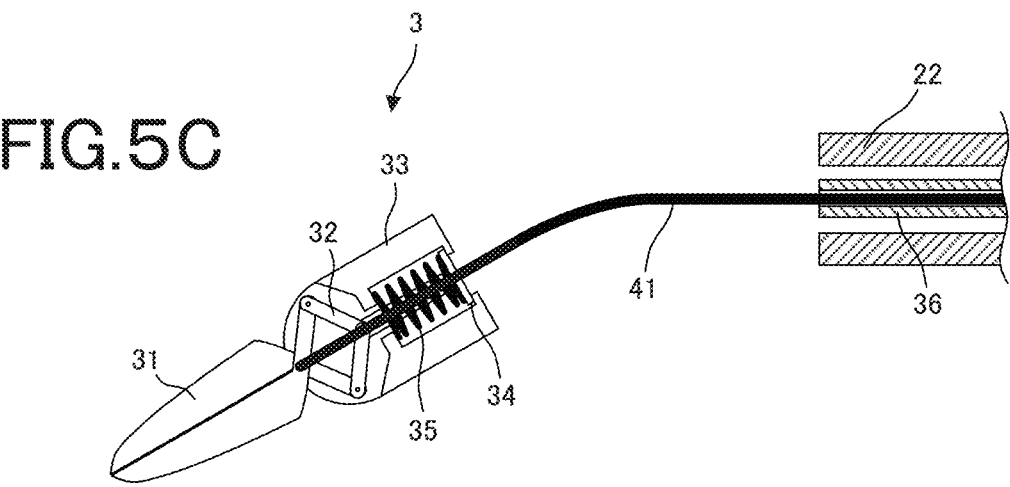

FIGS. 5A, 5B and 5C are illustrative of the holder assembly 3 in the surgical tool 1 according to the first embodiment.

The holder assembly 3 according to the first embodiment includes a gripper 31 that grips the tissue, a link member 32 that forms a link mechanism with the gripper 31, a forceps support member 33 capable of supporting the gripper 31 rotatably, a link support member 34 capable of supporting the link member 32 rotatably, an biasing member 35 for biasing the link support member 34, and a gripper opening/closing transmission member 36 for giving an urge to the link support member 34 against the biasing force of the biasing member 35.

The gripper 31 includes two members that are centrally supported in such a way as to be rotatable relative to the forceps support member 33, and its one end is supported in such a way as to be rotatable relative to the link member 32 while its other end is adapted to grip a tissue. The link member 32 includes two members and its one end supports the gripper 31 rotatably while its other end is rotatably supported by the link support member 34. The link support member 34 is supported in such a way as to be movable within the forceps support member 33, and energized by the biasing member 35 in a direction of closing the gripper 31. The gripper opening/closing transmission member 36 is pushed and pulled by operation of the gripper opening/closing member 52 shown in FIG. 1.

Referring typically to the holder assembly 3 according to the first embodiment, as the grip opening/closing member 52 is put from a normal state of FIG. 5A into operation, it causes a push to be given to the gripper opening/closing transmission member 36 so that the link support member 34 moves against the biasing member 35, whereupon the link member 32 moves so that the gripper 31 can be opened as shown in FIG. 5B.

Referring again to the holder assembly 3 according to the first embodiment, as the driving member 61a is rotated from the normal state of FIG. 5A to move the moving member 61b, it causes the wire 41 to be extended out relative to the shaft 22, as shown in FIG. 5C.

Figure 6:
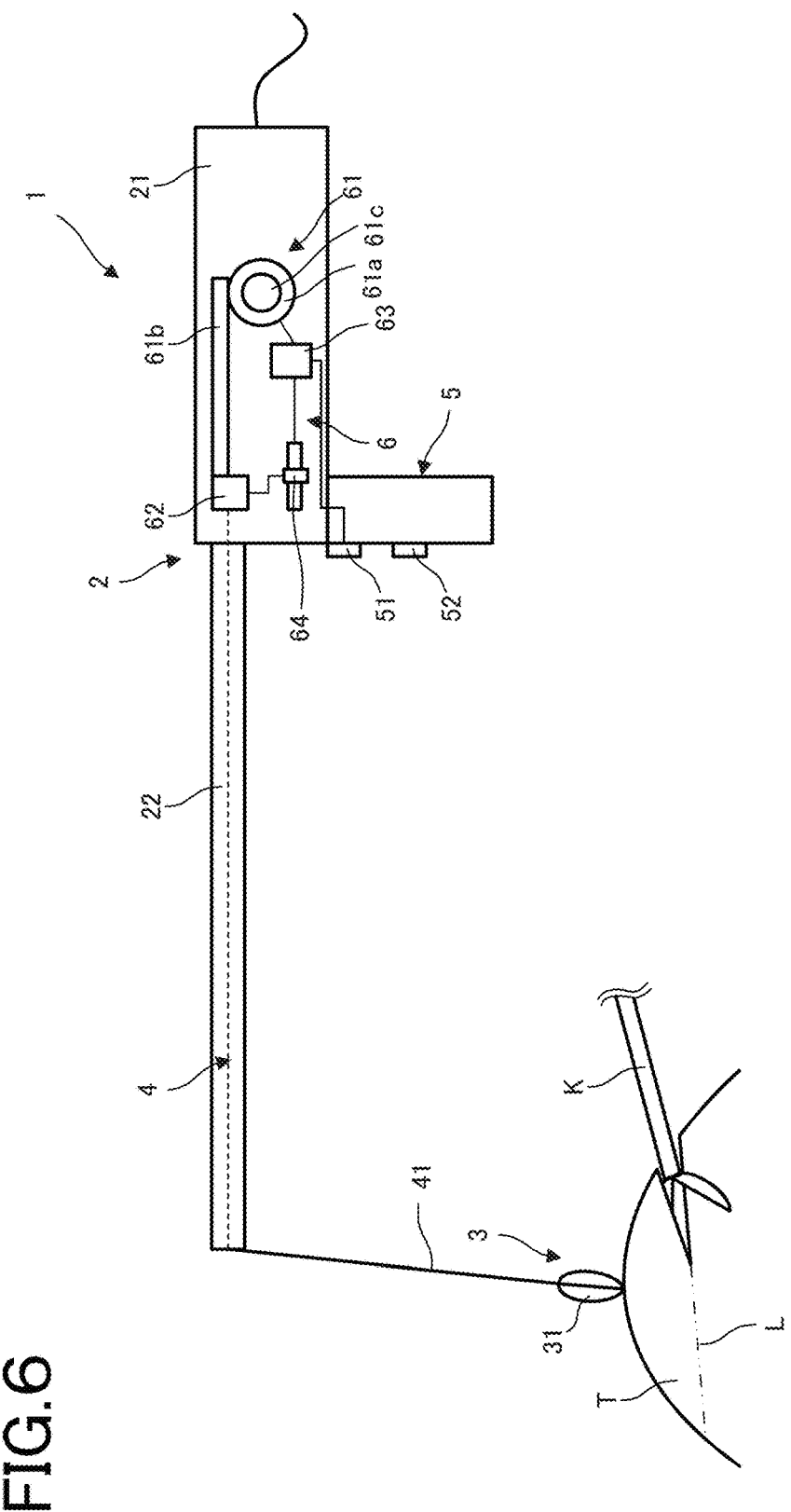
FIG. 6 is illustrative of the surgical tool 1 according to another example of the first embodiment.

FIG. 6 is illustrative of the surgical tool 1 according to another example of the first embodiment.

The surgical tool 1 of FIG. 6 includes a tension adjustor 64 that adjusts the tension of the connector 4. The tension applied on the wire 41 through the connector 4 is the sum of a force with which the tissue T to be peeled off along a peeling line L is gripped and lifted up and a tension applied on the peeling line L of the tissue T. For this reason, as the force of gripping and lifting up the tissue increases with a progress in peeling, it gives rise to a decrease in the tension applied on the peeling line L of the tissue T, rendering peeling difficult. If the tension applied on the wire 41 is operated by the tension adjustor 64, it is then possible to keep the tension applied on the peeling line L substantially constant. The tension adjustor 64 may detect the peeling position of the peeling line L by means of a sensor or the like for automatic adjustment or, alternatively, a practitioner may manually adjust the tension while viewing a display or the like not shown.

Figure 7:
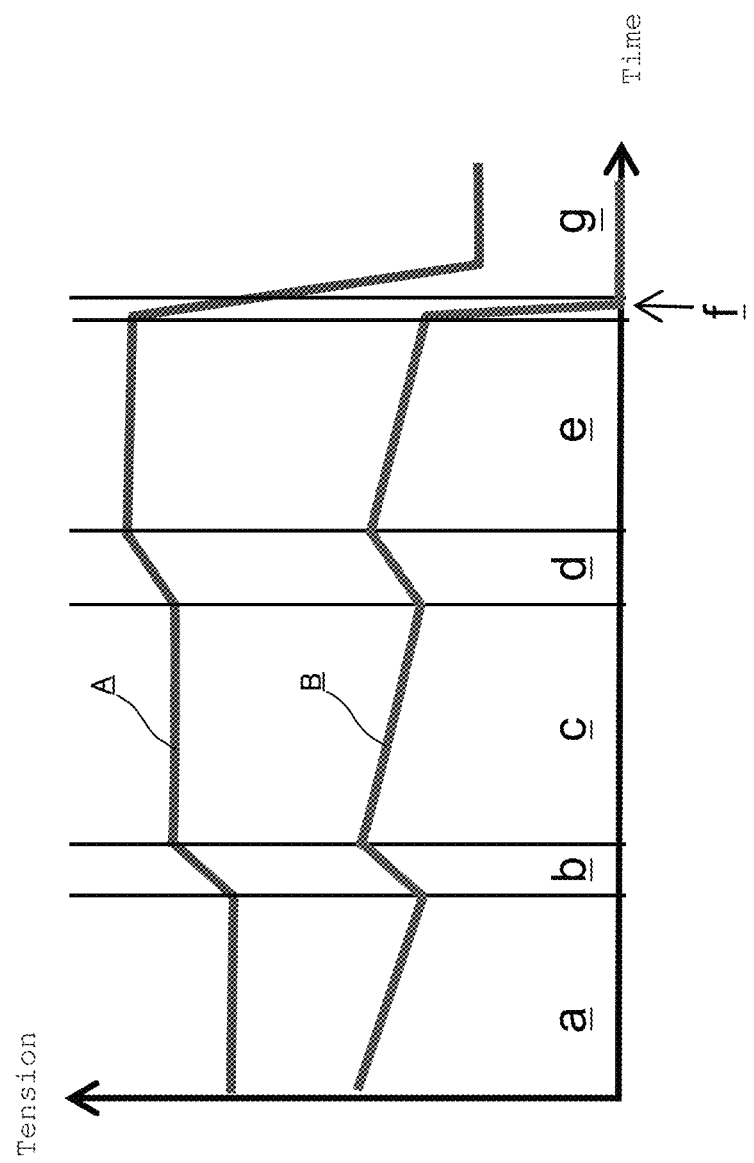
FIG. 7 is illustrative of one exemplary state of the tension of the surgical tool 1 according to another example of the first embodiment.

FIG. 7 is illustrative of a tension state in the surgical tool 1 according to another example of the first embodiment.

First of all, a tension is applied on the wire 41 in an area a to stop the movement of the shaft 22 in the tension holding mode, after which the tissue T is peeled off along the peeling line L by means of a peeling forceps K or the like. Although a tension A applied on the tension detector 62 is kept constant, a tension B applied on the peeling line L decreases gradually with an increasing tissue size. If a practitioner takes a look of the peeling line in an area b and judges the tension on the peeling line as decreasing, he or she then increases that tension by the tension adjustor 6. Likewise, a cycle of peeling off the tissue in area c, adjusting tension in area d and peeling off the tissue in area e is repeated. Finally, when the tissue is completely peeled off in an area f, there is an abrupt decrease in the tension. Here the tension detector 62 detects such an abrupt change to stop the movement of the wire 41. In an area g tissue peeling comes to an end and the movement of the wire 41 comes to a halt. Therefore, just only the weight of the peeled tissue is detected by the tension detector 62 as tension. Thereafter, the wire 41 is moved by the moving member 61*b* to bring the gripper 31 to a position where it comes in contact with the shaft 22 for tissue recovery.

Figure 8:
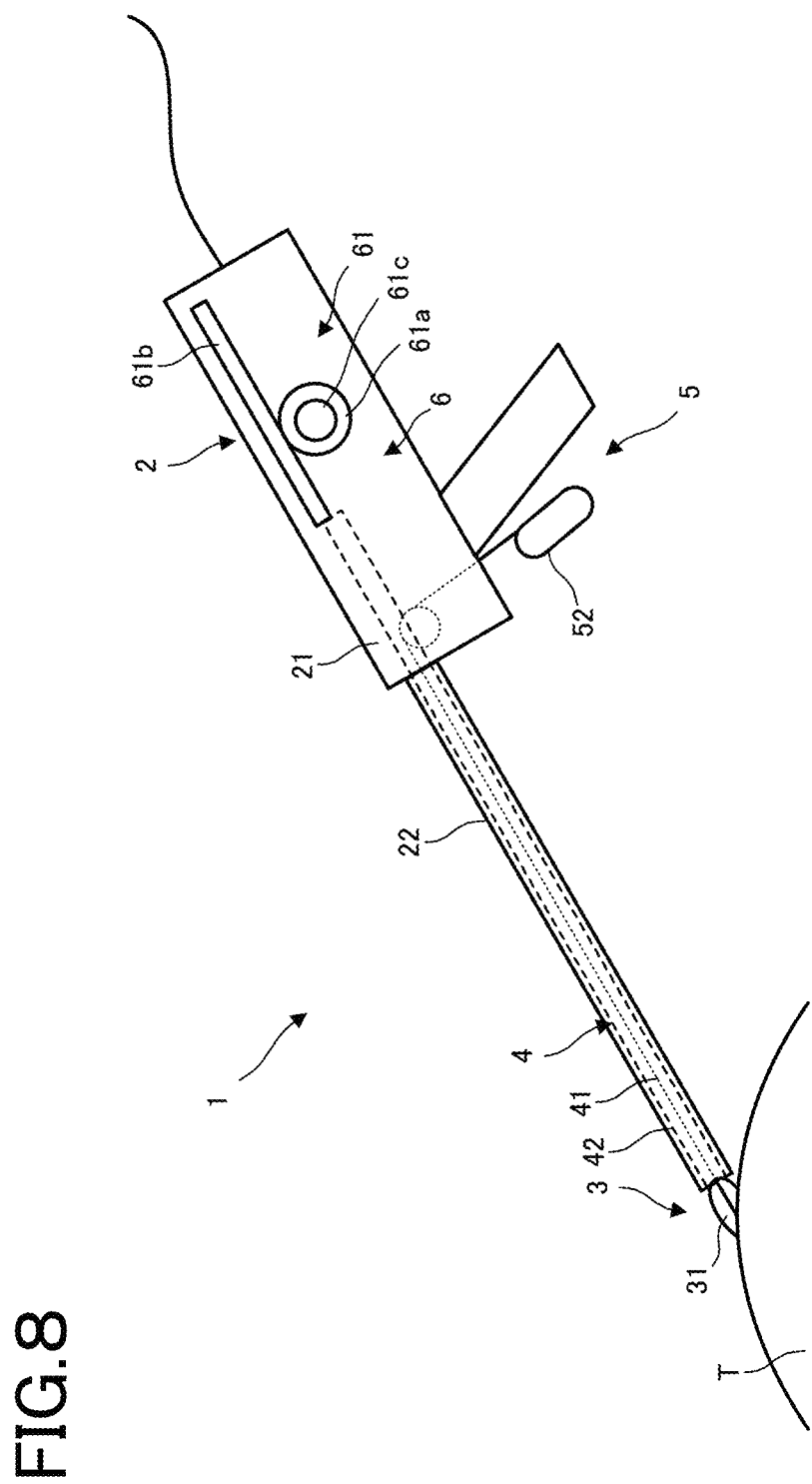
FIG. 8 shows the surgical tool according to the second embodiment.

FIG. 8 is illustrative of the surgical tool 1 according to the second embodiment.

The surgical tool 1 according to the second embodiment includes a main unit 2 including a case 21 and a hollow shaft 22 provided on the case 21, a holder assembly 3 for holding a living tissue T within the body cavity, a connector 4 that is inserted through the shaft 22 to connect the main unit 2 to the holder assembly 3, and a tension adjustor 6 that moves the connector 4 relative to the shaft 22 to make the tension of the connector 4 adjustable.

The connector 4 in the second embodiment includes a bendable elastic member 42. The elastic member 42 is capable of entering or leaving the shaft 22, and flexible by virtue of its elastic force. For instance, the elastic member 42 includes a coil tube or the like, through which the wire 41 of FIGS. 5A, 5B and 5C are passed. The operating unit 5 includes a gripper opening/closing member 52 to put the opening and closing of the gripper 31 into operation. The gripper opening/closing member 52 opens and closes the gripper 31 by pushing and pulling the wire 41. In the second embodiment, the gripper opening/closing member 52 is preferably constructed of a handle.

How to operate the surgical tool 1 according to the second embodiment will now be explained.

First of all, the gripper 31 is inserted through a trocar (not shown) in the abdominal cavity, and the gripper opening/closing member 52 is operated to open the gripper 31. After the gripper 31 inserted in the abdominal cavity is put over the tissue to be treated therein, it is closed by operation of the gripper opening/closing member 52 to grip the tissue T as shown in FIG. 8.

Figure 9:
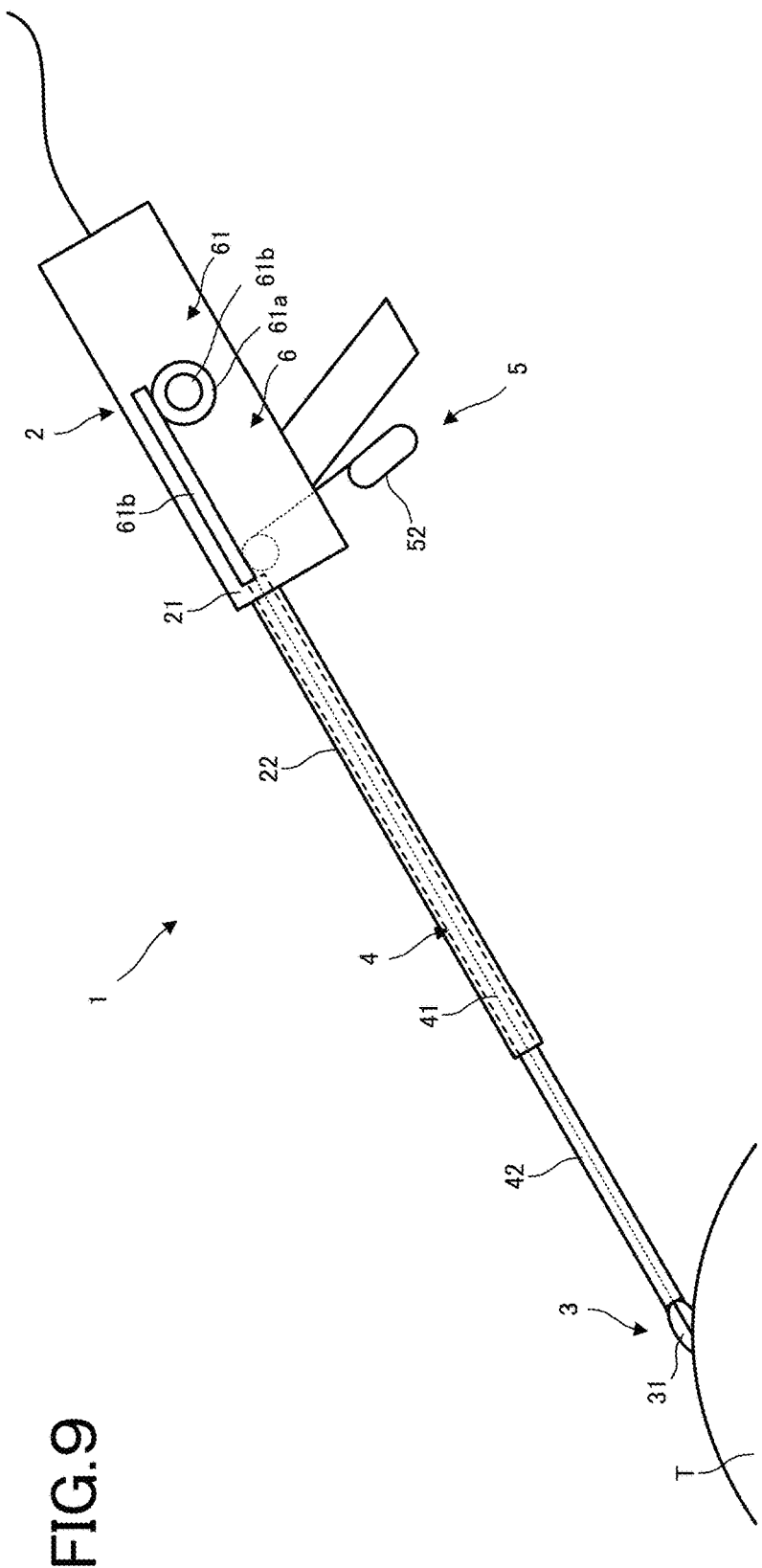
FIG. 9 shows that the elastic member is being let out of the surgical tool according to the second embodiment.

FIG. 9 shows that the elastic member 42 is being let out of the surgical tool 1 according to the second embodiment.

Subsequently, the elastic member 42 is let out while the tissue T is held by the gripper 31. The elastic member 42 may be let out by putting the drive operating portion 61*c* into operation whereby the driving member 61*a* is driven for movement of the moving member 61*b*.

Figure 10:
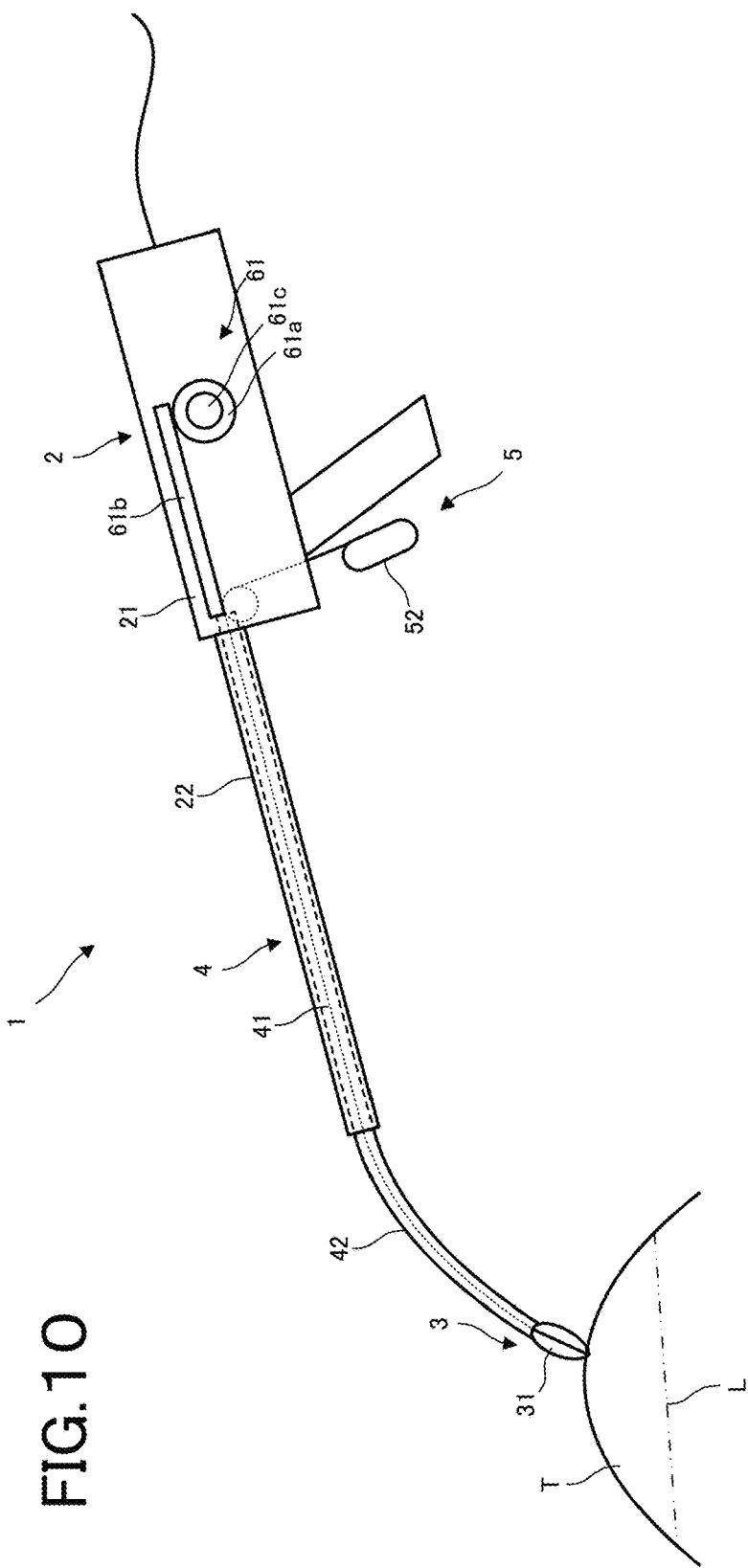
FIG. 10 shows that a tissue is being pulled by the surgical tool according to the second embodiment.

FIG. 10 shows that the tissue T is being pulled by the surgical tool 1 according to the second embodiment.

After the elastic member 42 is let out, the shaft 22 is lifted upward, and the movement of the shaft 22 is stopped in a position where the peeling line L of the tissue T is identifiable through an endoscope.

Figure 11:
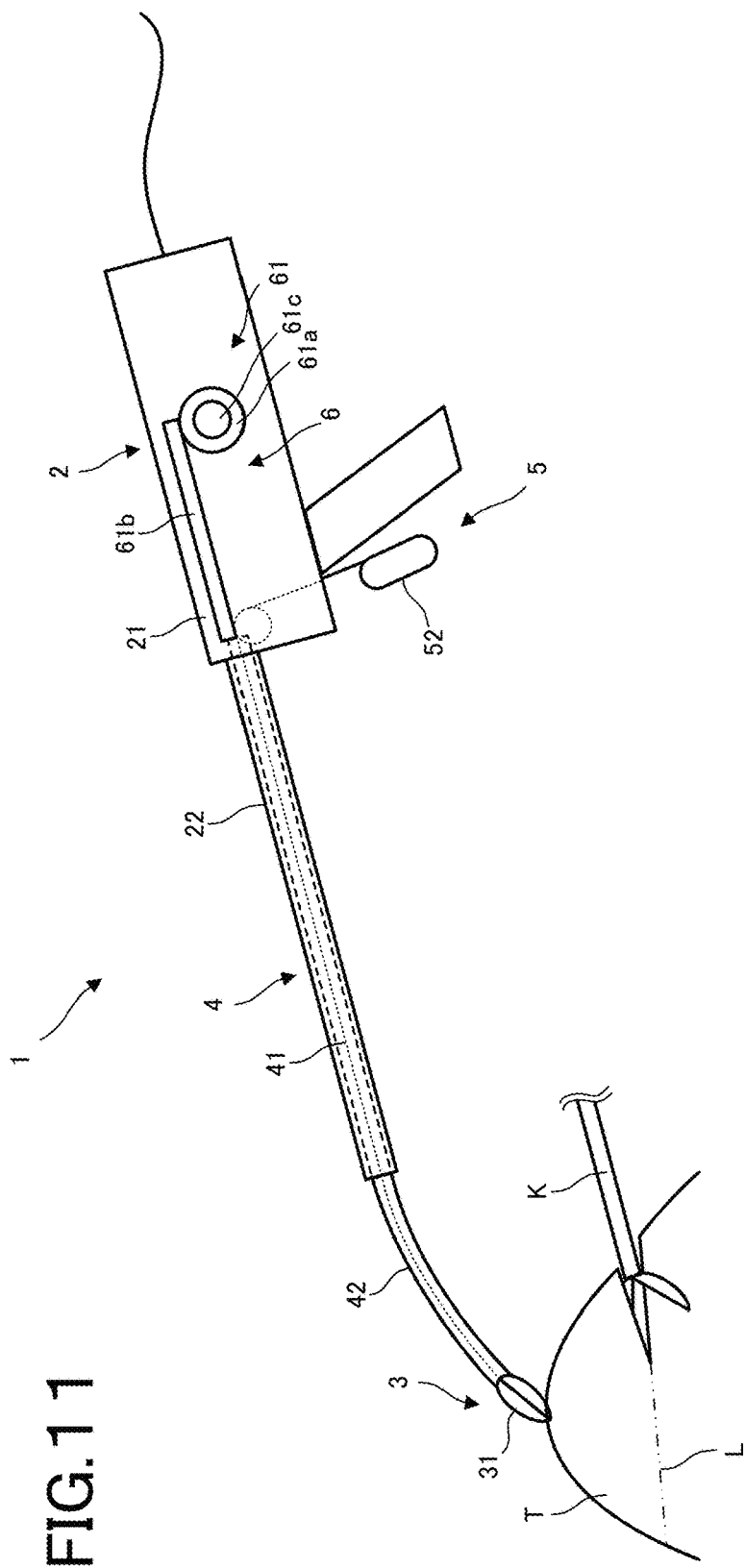
FIG. 11 shows that a tissue is being peeled off by the surgical tool according to the second embodiment.

FIG. 11 shows that the tissue T is being peeled off by the surgical tool 1 according to the second embodiment.

After the movement of the shaft 22 is stopped, the tissue T is peeled off along the peeling line L by means of a peeling forceps K or the like. With the surgical tool according to the second embodiment, as peeling progresses while the tissue T remains held, it causes the tissue T to be gradually pulled up by the elastic force of the elastic member 42 while it is peeled off with the result that the peeling line L is prevented from being hidden from view. It is thus possible to peel off the tissue T unerringly.

Figure 12:
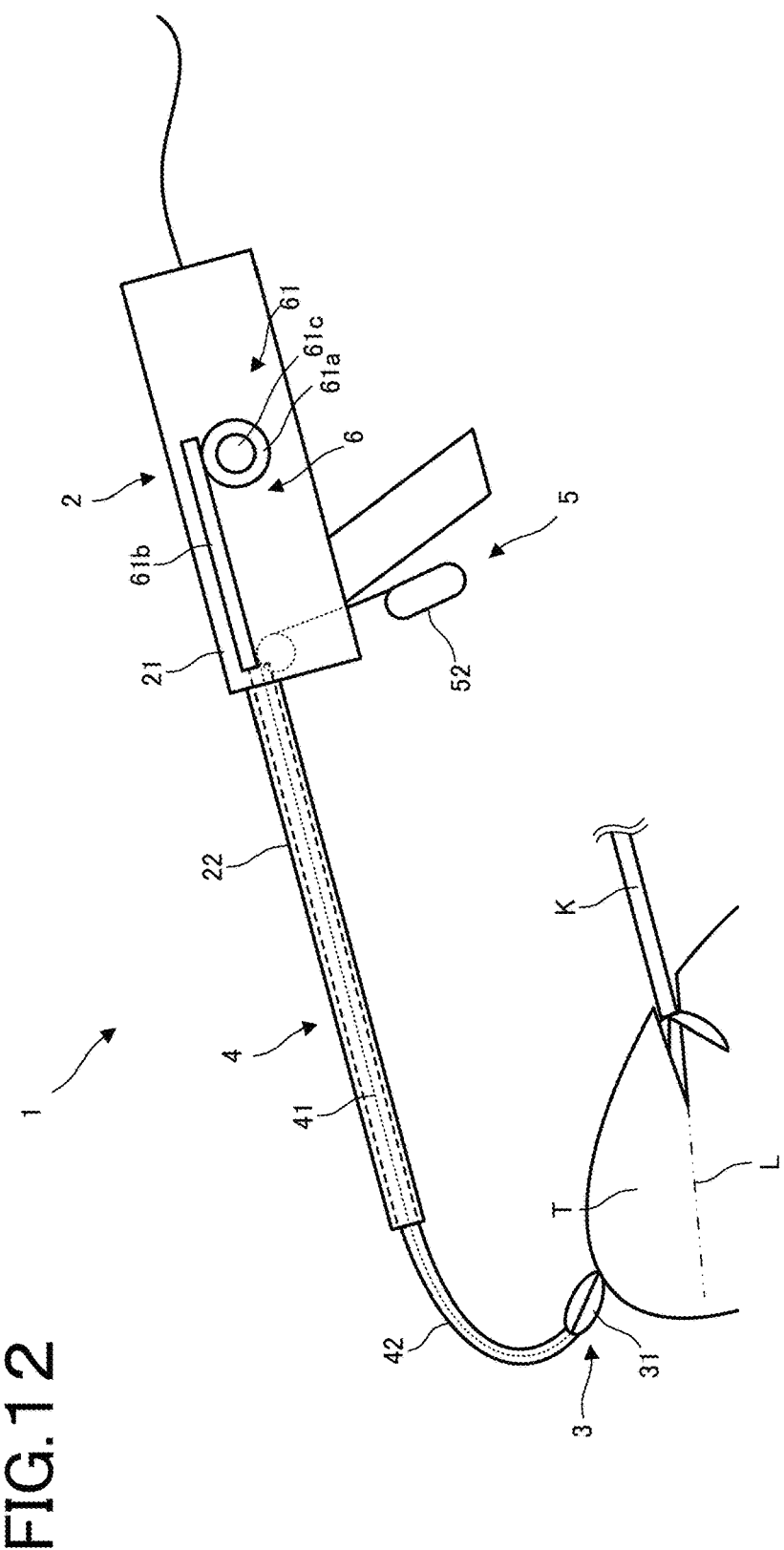
FIG. 12 is illustrative of another example of how to use the surgical tool according to the second embodiment.

FIG. 12 is illustrative of another example of how to use the surgical tool 1 according to the second embodiment.

With the surgical tool 1 according to the second embodiment, the elastic force of the elastic member 42 may be used to change the direction of pulling the tissue T. As shown typically in FIG. 12, the shaft 22 may be moved deep inside to pull the tissue T by the gripper 31 from the side opposite to the case 21. It is thus possible to create a space before the tissue T, viz., on the side of the case 21, in which space there is no or little interference occurring so that the peeling line L is easier to observe.

Figure 13:
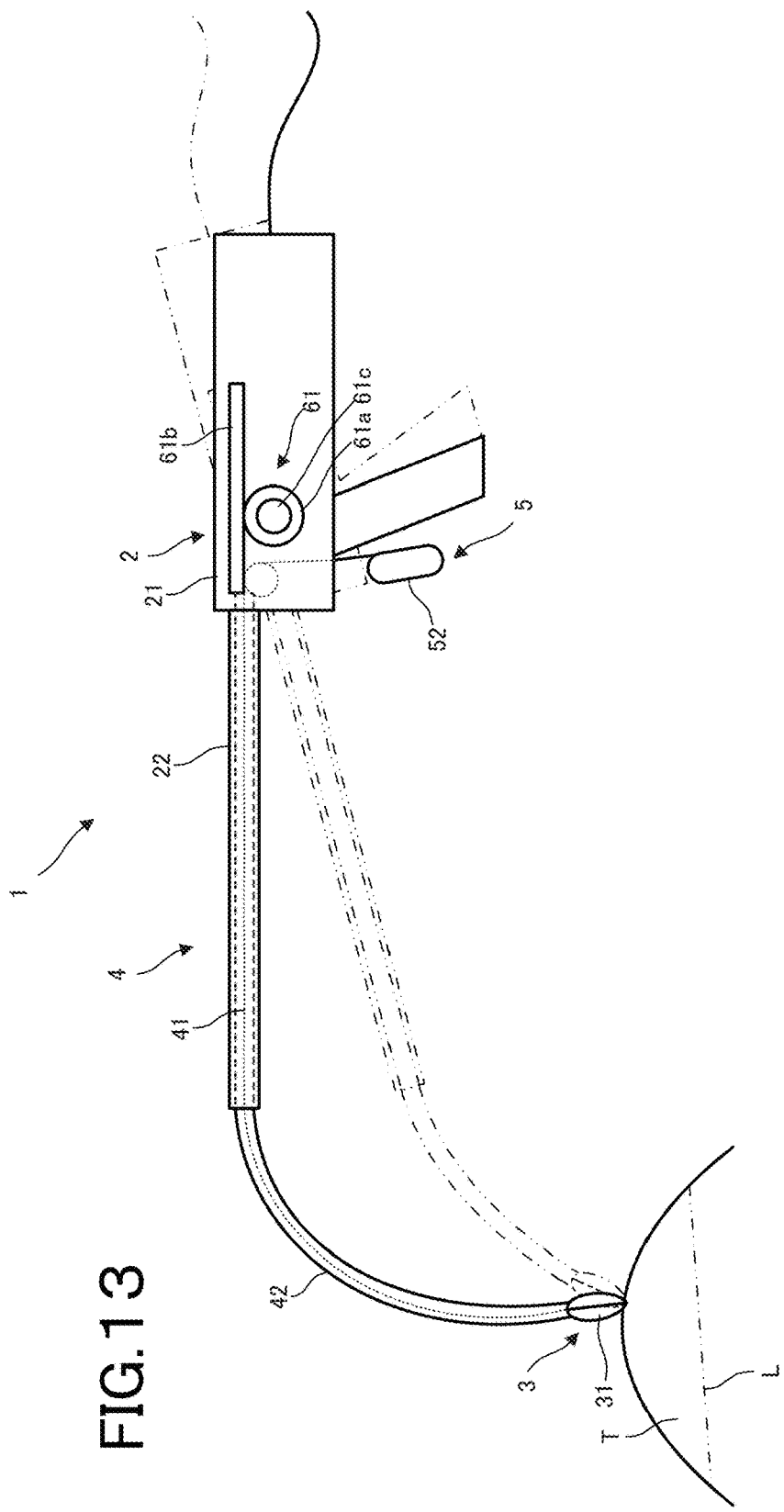
FIG. 13 is illustrative of yet another example of how to use the surgical tool according to the second embodiment.

FIG. 13 is illustrative of another example of how to use the surgical tool 1 according to the second embodiment.

With the surgical tool 1 of the second embodiment, it is possible to adjust the amount of withdrawal of the elastic member 42. When the amount of withdrawal the elastic member 42 increases as shown typically in FIG. 13, there may be a space created before the tissue T, viz., on the side of the case 21, in which space there is no or little interference occurring so that the peeling line L is easier to observe.

FIG. 14 is illustrative of the surgical tool according to the third embodiment of the invention.

In the surgical tool 1 according to the third embodiment, the section of the elastic member 42 is configured in such a way as to have anisotropy. In other words, the elastic member 42 according to the third embodiment has a difficult-to-bend direction and an easy-to-bend direction, and the direction of pulling the tissue T may be changed by rotation of the main unit 2. As shown typically in shown in FIG. 14, the elastic member 42 according to the third embodiment is configured in such a flat shape that its X-direction is longer than its Y-direction. The elastic member 42 is difficult to bend in the X-direction, but it is easy to bend in the Y-direction. Note here that the elastic member 42 is almost centrally provided with a hole 42*a* through which the wire 41 is passed.

Figure 15A:
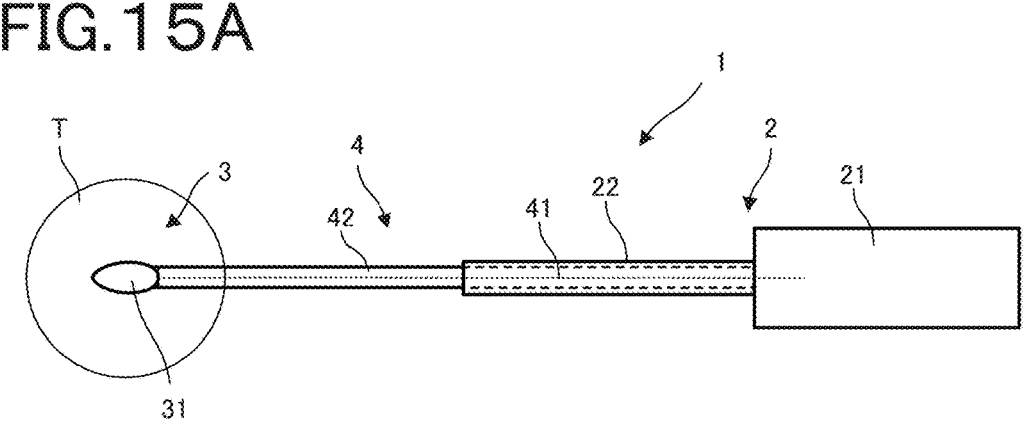
Figure 15B:
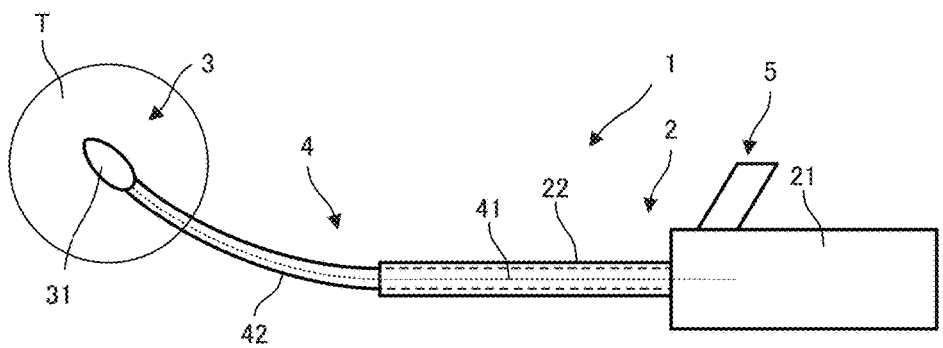
Figure 15C:
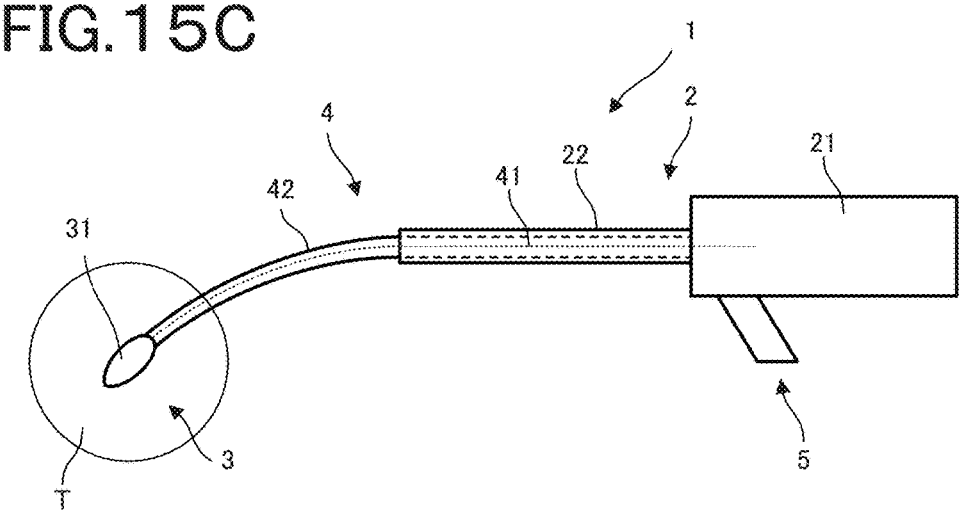

FIGS. 15A, 15B and 15C are a view of the surgical tool according to the third embodiment as viewed from above.

When the elastic member 42 in the surgical tool 1 according to the third embodiment is bent in the Y-direction, it looks like FIG. 15A as viewed from above.

When the main unit 2 of the surgical tool 1 in this state is rotated about the axis of the shaft 22 in the counter-clockwise direction as shown in FIG. 15B or in the clockwise direction as shown in FIG. 15C, there may be a space created before and above the tissue T, viz., above the case 21 side, in which space there is no or little interference so that the peeling line L is easier to observe.

FIG. 16 is illustrative of the surgical tool according to the fourth embodiment of the invention.

In the surgical tool 1 according to the fourth embodiment, the distal end of the holder assembly 3 in the first embodiment is configured as or provided with a hook 37.

The hook 37 is inserted into the abdominal cavity through a trocar (not shown). The hook 37 inserted into the abdominal cavity is received or caught on the tissue T to be treated therein. Then, the wire 41 is let out while the tissue T is caught by the hook 37. The wire 41 may be let out by putting the drive operating portion 61c into operation thereby driving the driving member 61a for movement of the moving member 61b.

After the wire 41 is let out, the shaft 22 is lifted upward, and the movement of the shaft 22 is stopped in a position where the peeling line L of the tissue T is identifiable by an endoscope. In that position, the tension holding mode operating member 51 is put into operation in the tension holding mode. After the movement of the shaft 22 is stopped to place the surgical tool in the tension holding mode, the tissue T is peeled off along the peeling line L by means of a peeling forceps K or the like.

Thus, the configuration of the distal end of the holder assembly 3 as the hook 37 allows the tissue T to be unerringly peeled off even in a narrow or limited space.

Figure 17:
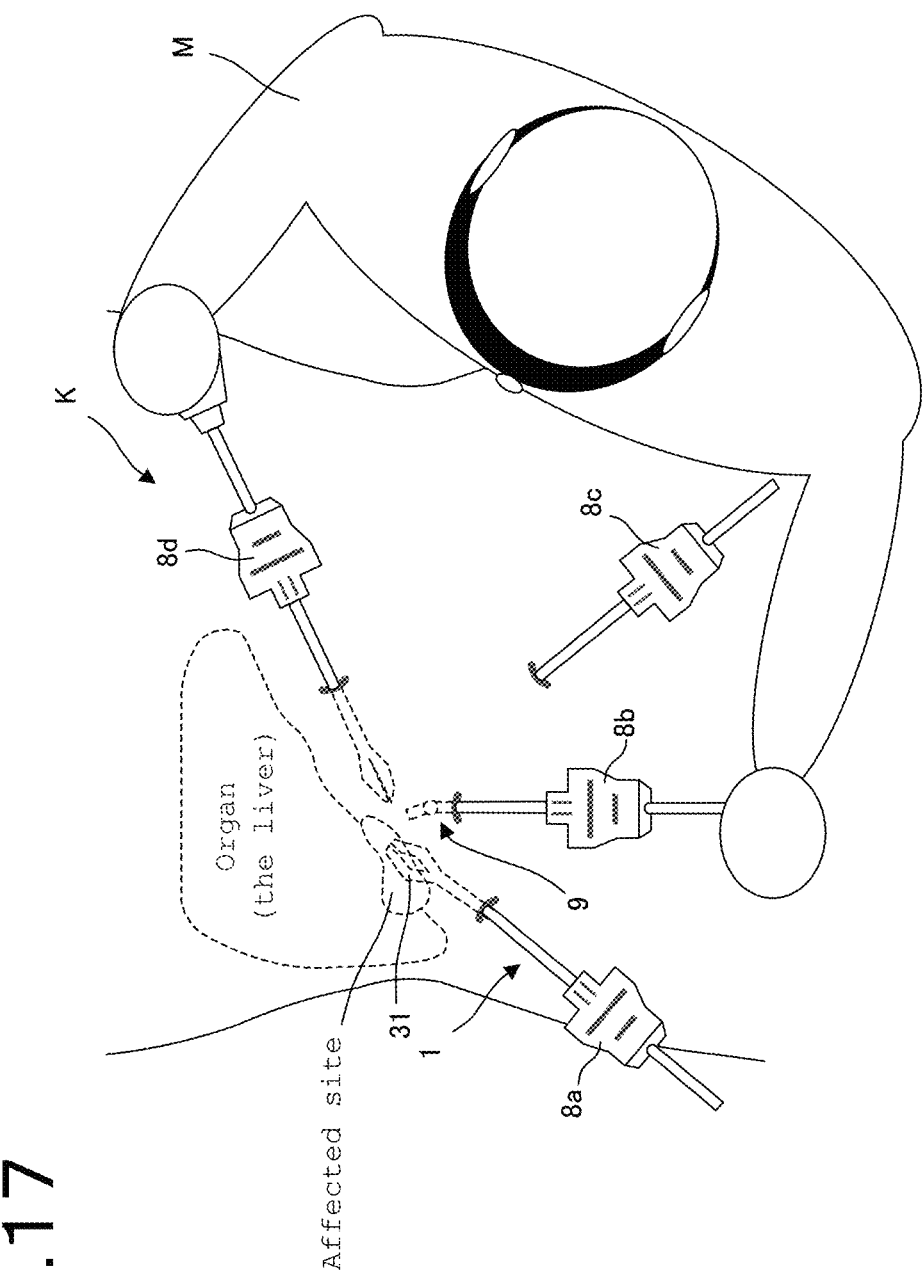
FIG. 17 is illustrative in schematic of one exemplary operation using the surgical tool embodied herein.

FIG. 17 is illustrative in schematic of one exemplary medical treatment using the surgical tool 1 described herein.

In laparoscopic surgery, tubes called trocars (channels) 8a to 8d are inserted through openings provided in the body wall of a patient, and various medical instruments are inserted through the trocars 8a to 8d into the body cavity of the patient. FIG. 17 is illustrative of a state where an endoscope 9 is inserted through the trocar 8b, a gripper 31 and such are inserted through the trocar 8a, and a peeling forceps K is inserted through the trocar 8d. The distal end of the endoscope 9 inserted through the trocar 8b into the body cavity of the patient is provided with an imaging device and a field-of-view adjustment mechanism capable of adjusting angles and suchlike to make affected sites or the holder assembly or the like come into view. The surgical tool 1 inserted through the trocar 8d into the body cavity of the patient is provided with a peeling forceps K, and a practitioner M operates the surgical tool 1 while adjusting the field-of-view adjustment mechanism of the endoscope 9 and viewing images taken of an affected site by the imaging device to open and close the gripper 31 for treatments of the affected site by the peeling forceps K.

The surgical tool 1 described herein includes a main unit 2 including a case 21 and a hollow shaft 22 provided on the case 21, a holder assembly 3 for holding a living tissue within the body cavity, a connector 4 that is inserted through the shaft 22 to connect the main unit 2 to the holder assembly 3, and a tension adjustor 6 that moves the connector 4 relative to the shaft 22 for adjustment of tension of the connector 4. It is thus possible to adjust the tension of the connector 4 that connects the holder assembly 3 for holding a tissue T to the main unit 2 so that the tissue T can be adjusted in an unerring state for unerring treatment, and interference of the surgical tool 1 with other one(s) can be avoided.

The surgical tool 1 described herein further includes an operating unit 5 for conversion to a tension holding mode in which the tension of the connector 4 is held, wherein the tension adjustor 6 holds the tension of the connector 4 in the tension holding mode. It is thus possible to hold the tension of the connector 4 in the tension holding mode so that the tissue T can be held in an unerring state for much more unerring treatment.

In the surgical tool 1 described herein, the tension adjustor 6 includes a driver 61 mounted in the case 21, a tension detector 62 that detects the tension of the connector 4, and a control unit 63 that controls the driver 61 on the basis of a value detected by the tension detector 62. It is thus possible to constantly pull the connector 4 under proper tension without budging the main unit 2.

According to the surgical tool 1 described herein, if the value detected by the tension detector 62 is judged as changing abruptly per unit time, the control unit 63 then deactivates the driving unit 61 so that there is no possibility that the holder assembly 3 may move abruptly, causing damages to the interior of the body cavity.

According to the surgical tool 1 described herein, when a first value decreasing abruptly per unit time is detected by the tension detector 62, the control unit 63 allows the connector 4 to be moved by the driver 61 toward the shaft 22 side for a constant time for the purpose of comparing the first value with a second value detected by the tension detector 62 after movement of the connector 4. When an increase in the amount of tension is less than a predetermined amount, the controller 63 deactivates the driver 61 so that even with the holder assembly 3 letting go of the tissue T, there is no damage done to the interior of the body cavity.

According to the surgical tool 1 described herein, the connector 4 includes a wire 41 that is extended out of the shaft, creating a space before the tissue T, viz., on the case 21 side, in which space there is no or little interference so that the tissue T is easy to observe.

According to the surgical tool 1 described herein, the connector 4 includes an elastic member 42 that is extended out of the shaft, creating a space before the tissue T, viz., on the case 21 side, in which space there is no or little interference so that the tissue T is easy to observe.

According to the surgical tool 1 described herein, the elastic member 42 has anisotropy so that just only by twisting the case 21 about the axial direction of the shaft 22, the position of the connector 4 can easily be changed.

According to the surgical tool 1 described herein, the holder assembly 3 includes a gripper 31 for gripping a living tissue T. It is thus possible to use a simple arrangement to hold the tissue T unerringly.

According to the surgical tool 1 described herein, the holder assembly 3 includes a hook 37 by which the living tissue T is caught. It is thus possible to hold the tissue T unerringly even in a limited space.

It is here to be appreciated that the invention is in no sense limited to such embodiments as described above. While the explanation of some embodiments embraces numerous specific details for illustration, it would be obvious to those skilled in the art that diverse variations or modifications made thereto are included within the scope of the invention. In other words, illustrative embodiments of the invention are described without excluding generality from the claimed inventions and imposing any limitation thereon.

REFERENCE SIGNS LIST

1: Surgical tool
2: Main unit
21: Case
22: Shaft
3: Holder assembly
31: Gripper
32: Hook
4: Connector
41: Wire 42: Elastic member
5: Operating unit
6: Tension adjustor
61: Driver
62: Tension detector
63: Control unit

The invention claimed is:

1. A surgical tool comprising:
    a main unit including a case and a hollow shaft provided on the case,
    a holder assembly for holding a living tissue within a body cavity, the holder assembly including a gripper,
    a tubular shaft that is inserted through the shaft so that when the holder assembly comes in contact with the shaft, the gripper being opened and closed depending on forward and backward movement of the tubular shaft,
    a wire configured to, separately from the tubular shaft, be inserted through the shaft to connect the main unit to the holder assembly,
    a driver that is provided on the case to cause forward and backward movement of the wire thereby varying a position of the holder assembly relative to a distal end of the shaft,
    a tension detector that detects a tension of the wire, and
    a controller configured to, when the holder assembly is separated from the distal end of the shaft, control the driver based on the tension detected by the tension detector.

2. The surgical tool according to claim 1, further including an operating unit having a holding mode operating member for selection to a tension holding mode in which the tension of the wire is held, and the controller controls the driver to hold the tension of the wire in the tension holding mode.

3. The surgical tool according to claim 1, wherein the controller deactivates the driver when the value sensed by the tension detector is judged as changing abruptly per unit time at the time a peeling of the tissue held by the holder assembly comes to an end.

4. The surgical tool according to claim 3, wherein the controller implements control such that when the tension detector detects a first detection value decreasing abruptly per unit time when the tissue is completely peeled off, the wire is moved by the driver to a shaft proximal side for a constant time, and a second detection value detected by the tension detector after the movement is compared with the first detection value so that when an increase in the amount tension is smaller than a predetermined amount, the driver is deactivated.

5. The surgical tool according to claim 1, wherein the holder assembly includes:
    a link that forms a link mechanism with the gripper,
    a housing for supporting the gripper at a distal end thereof,
    a link support for supporting the link, and
    a spring for biasing the link support in a direction of closing the gripper, wherein a tubular shaft opens the gripper by urging the link support against the biasing force of the spring.

* * * * *